United States Patent [19]

Iriuchijima et al.

[11] Patent Number: 4,855,311

[45] Date of Patent: Aug. 8, 1989

[54] BENZOISOTHIAZOLE OXIMES WHICH ARE PLANT PROTECTION AGENTS FOR CONTROL OF FUNGI AND BACTERIA

[75] Inventors: Shinobu Iriuchijima; Hirohiko Kobayashi, both of Yamato; Takahito Masuda, Machida; Shunnosuke Watanabe, Higashikurume; Hiroshi Tabata, Tokyo, all of Japan

[73] Assignees: Agro-Kanesho Co., Ltd.; Denki Kaguku Koygo Kabushiki Kaisha, both of Tokyo, Japan

[21] Appl. No.: 183,617

[22] Filed: Apr. 19, 1988

[30] Foreign Application Priority Data

Apr. 24, 1987 [JP] Japan ............................ 62-101513

[51] Int. Cl.$^4$ .................... A01N 43/80; C07D 275/06
[52] U.S. Cl. ...................................... 514/373; 548/210
[58] Field of Search .................... 548/210; 514/373

[56]  References Cited

U.S. PATENT DOCUMENTS

| 2,751,392 | 6/1956 | Grogan et al. | 548/210 |
| 3,629,428 | 12/1971 | Seki et al. | 548/210 |
| 4,666,930 | 5/1987 | Salzburg et al. | 514/373 |

FOREIGN PATENT DOCUMENTS

| 14301 | 5/1970 | Japan . | |
| 38080 | 12/1970 | Japan . | |
| 38356 | 12/1970 | Japan . | |
| 0014900 | 4/1971 | Japan | 548/210 |
| 1926 | 1/1972 | Japan . | |
| 37247 | 10/1974 | Japan . | |
| 0021673 | 2/1983 | Japan | 548/210 |

OTHER PUBLICATIONS

Hettler, Chemical Abstracts, vol. 65: 16956b-f (1966).
Hettler et al., Chemical Abstracts, vol. 66: 55431j (1967).
Hettler et al., Chemical Abstracts, vol. 70: 19973m (1969).

Primary Examiner—Anton H. Sutto
Assistant Examiner—Diana G. Rivers
Attorney, Agent, or Firm—Oblon, Spivak, McClelland, Maier & Neustadt

[57]  ABSTRACT

Derivatives of benzoisothiazole oxime which exhibit marked effect when used in plant protection agents for control of fungi and bacteria. They are of particular utility for the prevention of rice blast. The derivatives of benzothiazole oxime, according to this invention, are represented by the following general formula (I):

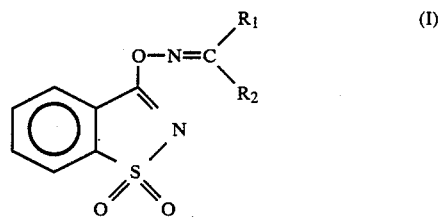

wherein $R_1$ is an alkyl group, and $R_2$ is an alkyl, alkenyl, alkoxyalkyl or alkoxycarbonyl group, where $R_1$ and $R_2$ may be coupled together to form an alkylene chain.

31 Claims, No Drawings

BENZOISOTHIAZOLE OXIMES WHICH ARE PLANT PROTECTION AGENTS FOR CONTROL OF FUNGI AND BACTERIA

BACKGROUND OF THE INVENTION

1. Field of the Invention

The present invention relates to novel compounds which are derivatives of benzoisothiazole oxime, a process for preparing the same and plant protection agents for control of fungi and bacteria containing, as an effective component, at least one of said derivatives of benzoisothiazole oxime.

2. Prior Art Statement

Japanese Patent Publication Nos. 38080/1970, 38356/1970 and 37247/1974 disclose that certain benzoisothiazole system compounds are useful for control of fungi and bacteria in agricultural and like applications. However, the results of appraisal tests on the effects of these known compounds to plants reveal that further improvements thereof are desirous.

OBJECT AND SUMMARY OF THE INVENTION

It is, therefore, a principal object of this invention to provide novel benzoisothiazole system compounds which are useful for the argricultural and floricultural applications.

Another object of this invention is to provide improved plant protection agents for control of fungi and bacteria, which contain the aforementioned benzoisothiazole compounds and exhibit marked effectiveness.

We have made studies to find a compound which is harmless to rice plants and yet effective for the prevention of rice blast, one of the most serious problems in the growing of rice in paddy fields. Through our study we found that certain novel derivatives of benzoisothiazole oxime (hereinafter referred to as "compounds of this invention") exhibited superior effect of preventing rice blast when they were applied to soil or applied through foliar application and that they were harmless to rice plants grown either in a dry field or in a paddy field. The present invention has been accomplished on the basis of the aforementioned result of our study. Accordingly, the present invention provides novel derivatives of benzoisothiazole oxime represented by the following general formula (I):

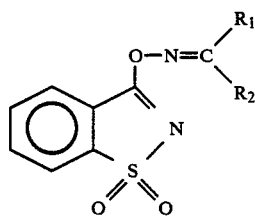
(I)

wherein $R_1$ is an alkyl group, and $R_2$ is an alkyl, alkenyl, alkoxyalkyl or alkoxycarbonyl group, where $R_1$ and $R_2$ may be coupled together to form an alkylene chain.

Also provided by this invention is a process for preparing derivatives of benzoisothiazole oxime represented by the general formula (I), the process comprising the step of reacting 3-halo-1,2-benzoisothiazole 1,1-dioxide represented by the following general formula (II):

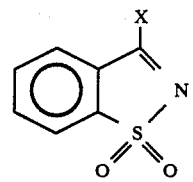
(II)

wherein X is a chlorine or bromine atom; with an oxime represented by the following general formula (III):

(III)

wherein $R_1$ and $R_2$ are the same as defined above.

Also included in the spirit and scope of the invention are a plant protection agent containing, as an effective component, at least one of the aforementioned derivatives of benzoisothiazole oxime represented by the general formula (I):

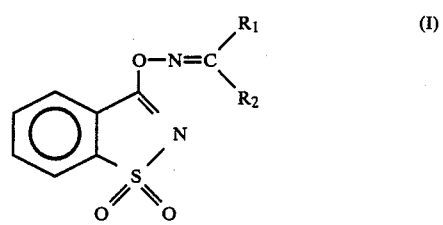
(I)

and a method of prevention of rice blast by the application thereof.

DESCRIPTION OF THE INVENTION

The present invention will now be described in detail.

The compounds of this invention may be prepared by the process represented by the following reaction formula (wherein $R_1$, $R_2$ and X are the same as defined above).

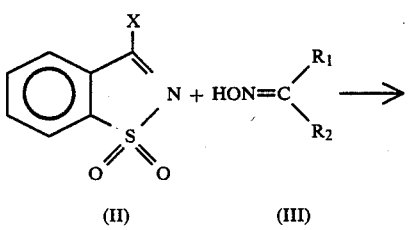

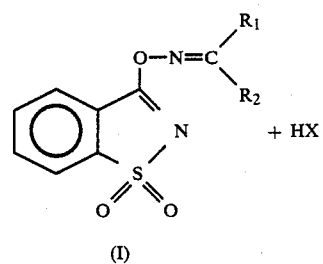

The 3-halo-1,2-benzoisothiazole 1,1-dioxides represented by the general formula (II), which are used as the starting materials for the compounds of this invention, are known in the art. (Detailed descriptions of 3-halo- 1,2-benzoisothiazole 1,1-dioxides can be found, for example, in the specifications of Japanese Patent Publication Nos. 14301/1970 and 1926/1972. These prior patent publications are incorporated herein as references.) The other starting materials which are used to react with the 3-halo-1,2-benzoisothiazole 1,1-dioxides are oximes represented by the general formula (III), and may be easily synthesized by reacting ketones with hydroxylamine. In the general formula (III), $R_1$ is an alkyl group including, for example, methyl, ethyl, propyl, isopropyl, butyl, isobutyl, t-butyl, pentyl and hexyl groups. In the general formula (III), $R_2$ may be an alkyl group such as methyl, ethyl, propyl, isopropyl, butyl, isobutyl, t-butyl, pentyl and hexyl; an alkenyl group such as vinyl and 3-butenyl; an alkoxyalkyl group such as methoxymethyl, ethoxymethyl and 2-methoxyethyl; and alkoxycarbonyl group such as methoxycarbonyl and ethoxycarbonyl. The groups $R_1$ and $R_2$ may be coupled together to form an alkylene chain, such as tetramethylene or pentamethylene chain.

It is desirous that the reaction is performed in the presence of a solvent. A wide variety of non-protonic solvents may be used singly or in combination in the practice of the reaction; examples being hydrocarbons such as cyclohexane, benzene and toluene; halogenated hydrocarbons such as chloroform, methylene chloride, carbon tetrachloride, trichloroethane and chlorobenzene; ethers such as diethyl ether, dibutyl ether, dioxane and tetrahydrofuran; ketones such as acetone and methyl ethyl ketone; acid amides such as dimethylformamide and dimethylacetamide; sulfur-containing solvents such as sulfolanes and dimethyl sulfoxide; nitriles such as acetonitrile and propionitrile; and esters such as ethyl acetate and amyl acetate.

In practice of the process of this invention, 3-halo-1,2-benzoisothiazole 1,1-dioxide represented by the general formula (II) is dissolved or suspended in one or more of the aforementioned solvents, and reacted with an oxime represented by the general formula (III) by adding the oxime to the solution or suspension directly or as a solution or suspension in a solvent. When it is desired to promote the reaction or to neutralize hydrogen halide formed by the reaction, one or more of basic materials may be used. Examples of such basic materials include organic bases such as triethylamine, tributyl amine and pyridine; hydroxides of alkali or alkaline earth metals, such as sodium hydroxide, potassium hydroxide and calcium hydroxide; carbonates of alkali or alkaline earth metals, such as sodium carbonate, sodium hydrogen carbonate and calcium carbonate; basic polymers such as strongly basic resins having quaternary ammonium structure, weekly basic resins having tertiary amine structure and resins having pyridine structure. Preferable basic materials are organic bases, such as triethylamine and tributylamine.

The reaction proceeds generally at room temperature without the need of cooling or heating. However, the reaction is exothermic and it is desirous to cool the reaction mixture to between 0° C. and 20° C., particularly when the reaction product is unstable at high temperature. After the completion of reaction, the by-product hydrogen halide or a salt thereof is removed by rinsing with water or filtration to obtain a compound of this invention.

Typical examples of the compound of this invention will be listed in the following Table 1. However, it is to be noted here that the invention is not limited only to the compounds shown in Table 1.

TABLE 1

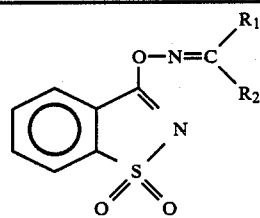

| Compound No. | $R_1$ | $R_2$ | Physical Constant |
|---|---|---|---|
| 1 | —CH₃ | —CH₃ | mp 190–193° C. |
| 2 | —CH₃ | —CH₂CH₃ | mp 140–141° C. |
| 3 | —CH₃ | —CH(CH₃)₂ | mp 119° C. |
| 4 | —CH₃ | —CH₂CH(CH₃)₂ | mp 139–140° C. |
| 5 | —CH₃ | —COOCH₃ | mp 193–196° C. |
| 6 | —CH₃ | —CH₂CH₂CH=CH₂ | mp 105–106° C. |
| 7 | —CH₃ | —C(CH₃)₃ | mp 97° |
| 8 | —CH₃ | —CH₂—O—CH₃ | mp 80° C. |
| 9 |  | —(CH₂)₄— | mp 140° C. |
| 10 |  | —(CH₂)₅— | mp 140–142° C. |
| 11 | —C₂H₅ | —C₂H₅ | mp 140–141° C. |
| 12 | —CH₃ | —CH=CH₂ | mp 163–164° C. |

The compounds of this invention may be used directly as plant protection agents for control of fungi and bacteria. However, it is a common practice either to dissolve or disperse them in an appropriate liquid carrier, for example, in an organic solvent or to mix them with or have them absorbed by a solid carrier, for example, a diluent or filler. The compounds of this invention may be formulated by the addition of a variety of auxiliary agents, such as emulsifiers, stabilizers, dispersing agents, suspending agents, wetting agents or penetrating agents, to form emulsions, wettable powders, granules and powders. The thus formulated plant protection agents may be applied so that 1 g to 1000 g, preferably 50 g to 500 g of the effective component is applied to 10 ares. For the purpose of reducing the labor for application thereof or for preventing further blights caused by various fungi and bacteria, other germicides or insecticides may be mixed therewith.

The present invention will now be described more specifically with reference to some examples thereof. However, it is to be noted that the invention is not limited only to the following examples.

EXAMPLE 1

Synthesis of 3-(2-propaneiminoxy)-1,2-benzoisothiazole 1,1-dioxide (Compound No. 1)

A suspension of 3-chloro-1,2-benzoisothiazole 1,1-dioxide (2.02 g, 10 millimoles) in toluene (20 ml) was stirred under cooling in a water bath. To the suspension was added acetone oxime (0.765 g, 10.5 millimoles), and the mixture was stirred for 10 minutes. To the mixture was added water under agitation. The precipitated crystals were collected with filtration, rinsed with water, and then dried in vacuum at 40° to 50° C. to give 1.84 g (Yield: 77%) of the object compound. The compound was recrystallized with acetone.

Melting Point: 190°–193° C.
Infrared Absorption Spectrum ($\nu^{nujol}$ cm$^{-1}$): 1617, 1553, 1321, 1168.
Nuclear Magnetic Resonance Spectrum (CDCl₃) δ: 2.16 (3H, s), 2.21 (3H, s), 7.78 (4H, m).

EXAMPLE 2

Synthesis of 3-(cyclohexaneiminoxy)-1,2-benzoisothiazole 1,1-dioxide (Compound No. 10)

A suspension of 3-chloro-1,2-benzoisothiazole 1,1-dioxide (2.02 g, 10 millimoles) in toluene (20 ml) was agitated under cooling in a water bath. Triethylamine (1.11 g, 11 millimoles) and then cyclohexanone oxime (1.19 g, 10.5 millimoles) were added to the suspension. The mixture was stirred for 15 minutes, and then water was added and the mixture agitated for additional 5 minutes. The precipitated crystals were collected through a glass filter, rinsed with water, and then dissolved in acetone under heating. The solution in acetone was cooled on an ice bath to give 1.81 g (Yield: 65%) of the recrystallized object compound.
Melting Point: 140°–142° C.
Infrared Absorption Spectrum ($\nu^{nujol}$ cm$^{-1}$):
1615, 1557, 1172.
Nuclear Magnetic Resonance Spectrum (CDCl$_3$) δ:
1.73 (6H, br s), 2.2–2.9 (4H), 7.67 (4H, m).

EXAMPLE 3

Synthesis of 3-(1-methoxycarbonyl-1-ethaneiminoxy)-1,2-benzoisothiazole 1,1-dioxide (Compound No. 5)

A solution of 3-chloro-1,2-benzoisothiazole 1,1-dioxide (2.02 g, 10 millimoles) in dioxane (25 ml) was agitated under cooling in a water bath. Triethylamine (1.11 g, 11 millimoles) and then methyl 2-(hydroxyimino)propionate (1.29 g, 11 millimoles) were added to the solution, and the mixture was stirred for 30 minutes. Water (50 ml) was added and the mixture agitated for additional 5 minutes. The precipitated crystals were collected with filtration and rinsed with water. The filtered crystals were recrystallized with acetone to give 1.83 g (Yield: 65%) of the object compound.
Melting Point: 193°–196° C.
Infrared Absorption Spectrum ($\nu$ $^{nujol}$ cm$^{-1}$):
1748, 1735, 1619, 1560, 1365, 1325, 1291, 1170.
Nuclear Magnetic Resonance Spectrum (CD$_3$SOCD hd 3) δ:
2.43 (3H, s), 3.87 (3H, s), 8.0(4H, m).

EXAMPLE 4

Synthesis of 3-(5-hexene-2-iminoxy)-benzoisothiazole 1,1-dioxide (Compound No. 6)

In a manner similar to that in Example 2 except that 5-hexene-2-one oxime (1.36 g, 12 millimoles) was used in place of the cyclohexanone oxime, 1.80 g (Yield: 65%) of the object compound was obtained.
Melting Point: 105°–106° C.
Infrared Absorption Spectrum ($\nu$ $^{nujol}$ cm$^{-1}$):
1612, 1553, 1331, 1166.
Nuclear Magnetic Resonance Spectrum (CDCl$_3$) δ:
2.17 (3H, s), 2.50 (4H, m), 4.87–5.27 (2H), 5.5–6.1 (1H), 7.75 (4H, m).

EXAMPLE 5

Synthesis of 3-(3-pentaneiminoxy)-1,2-benzoisothiazole 1,1-dioxide (Compound No. 11)

In a manner similar to that in Example 2 except that pentane-3-one oxime (1.06 g, 10.5 millimoles) was used in place of cyclohexanone oxime, 1.62 g (Yield: 64%) of the object compound was obtained.
Melting Point: 140°–141° C.
Infrared Absorption Spectrum ($\nu$ $^{nujol}$ cm$^{-1}$):
1619, 1559, 1330, 1168.
Nuclear Magnetic Resonance Spectrum (CDCl$_3$) δ:
1.27 (6H, t, J=7.5 Hz), 2.48 (2H, q, J=7.5 Hz), 2.62 (2H, q, J=7.5 Hz), 7.73 (4H, m).

EXAMPLE 6

Synthesis of 3-(2-butaneiminoxy)-1,2-benzoisothiazole 1,1-dioxide (Compound No. 2)

In a manner similar to that in Example 2 except that 2-butanone oxime (0.92 g, 10.6 millimoles) was used in place of cyclohexanone oxime, 1.04 g (Yield: 41%) of the object compound was obtained.
Melting Point: 140°–141° C.
Infrared Absorption Spectrum ($\nu$ $^{nujol}$ cm$^{-1}$):
1620, 1560, 1325, 1171.
Nuclear Magnetic Resonance Spectrum (CDCl$_3$) δ:
1.20 (3H, t, J=7.5 Hz), 2.17 (3H, s), 2.48 (2H, q, J=7.5 Hz), 7.70 (4H, m).

EXAMPLE 7

Synthesis of 3-(4-methylpentane-2-iminoxy)-1,2-benzoisothiazole 1,1-dioxide (Compound No. 4)

In a manner similar to that in Example 2 except that 4-methyl-2-pentanone oxime (1.27 g, 11 millimoles) was used in place of cyclohexanone oxime, 1.03 g (Yield: 37%) of the object compound was obtained.
Melting Point: 139°–140° C.
Infrared Absorption Spectrum ($\nu$ $^{nujol}$ cm$^{-1}$):
1615, 1555, 1340, 1310, 1170, 940, 830, 770.
Nuclear Magnetic Resonance Spectrum (CDCl$_3$) δ:
1.02 (6H, d, J=6 Hz), 2.15 (3H, s), 2.0–2.5 (3H), 7.75 (4H, m).

EXAMPLE 8

Synthesis of 3-(3-methylbutane-2-iminoxy)-1,2-benzoisothiazole 1,1-dioxide (Compound No. 3)

In a manner similar to that in Example 2 except that 3-methyl-2-butanone oxime (1.11 g, 11 millimoles) was used in place of cyclohexanone oxime, 2.08 g (Yield: 78%) of the object compound was obtained.
Melting Point: 119° C.
Infrared Absorption Spectrum ($\nu$ $^{nujol}$ cm$^{-1}$):
1625, 1565, 1330, 1310, 1165, 940, 840.
Nuclear Magnetic Resonance Spectrum (CDCl$_3$) δ:
1.23 (6H, d, J=6 HZ), 2.13 (3H, s), 2.87 (1H, septet, J=6Hz), 7.73 (4H, m).

EXAMPLE 9

Synthesis of 3-(cyclopentaneiminoxy)-1,2-benzoisothiazole 1,1-dioxide (Compound No. 9)

In a manner similar to that in Example 2 except that cyclopentanone oxime (1.10 g, 11 millimoles) was used in place of cyclohexanone oxime, 1.98 g (Yield: 75%) of the object compound was obtained.
Melting Point: 140° C.
Infrared Absorption Spectrum ($\nu$ $^{nujol}$ cm$^{-1}$):
1625, 1555, 1330, 1300, 1170, 940, 810, 780.
Nuclear Magnetic Resonance Spectrum (CDCl$_3$) δ:
1.9 (4H, m), 2.6 (4H, m), 7.6 (4H, m).

EXAMPLE 10

Synthesis of
3-(3,3-dimethylbutane-2-iminoxy)-1,2-benzoisothiazole
1,1-dioxide (Compound No. 7)

In a manner similar to that in Example 2 except that 3,3-dimethyl-2-butanone oxime (1.27 g, 11 millimoles) was used in place of cyclohexanone oxime, 1.69 g (Yield: 60%) of the object compound was obtained.
Melting Point: 97° C.
Infrared Absorption Spectrum ($\nu$ $^{nujol}$ cm$^{-1}$):
1610, 1560, 1325, 1170, 940, 850, 820, 780.
Nuclear Magnetic Resonance Spectrum (CDCl$_3$) $\delta$:
1.3 (9H, s), 2.15 (3H, s), 7.7 (4H, m).

EXAMPLE 11

Syntheis of
3-(1-methoxy-2-propaneiminoxy)-1,2-benzoisothiazole
1,1-dioxide (Compound No. 8)

In a manner similar to that in Example 2 except that 1-methoxy-2-propanone oxime (1.10 g, 11 millimoles) was used in place of cyclohexanone oxime and that the reaction was carried out under ice-water cooling, 1.74 g (Yield: 60%) of the object compound was obtained.
Melting Point: 80° C.
Infrared Absorption Spectrum ($\nu$ nujol cm$^{-1}$):
1620, 1560, 1325, 1170, 1110, 950, 850, 770.
Nuclear Magnetic Resonance Spectrum (CDCl$_3$) (main
isomer) $\delta$:
2.23 (3H, s), 3.35 (3H, s) 4.15 (2H, s) 7.7 (4H, m).

EXAMPLE 12

Synthesis of
3-(3-butene-2-iminoxy)-1,2-benzoisothiazole 1,1-dioxide
(Compound No. 12)

In a manner similar to that in Example 2 except that 3-butene-2-one oxime (0.935 g, 11 millimoles) was used in place of cyclohexanone oxime, 1.60 g (Yield: 64%) of the object compound was obtained.
Melting Point: 163°-164° C.
Infrared Absorption Spectrum ($\nu$ $^{nujol}$ cm$^{-1}$):
1615, 1555, 1330, 1170, 950, 870, 770.
Nuclear Magnetic Resonance Spectrum (CDCl$_3$) $\delta$:
2.33 (3H, s), 5.77 (1H, d, J=11 Hz), 5.93 (1H, d, J=17 Hz), 6.7 (1H, dd, J=11, 17 Hz), 7.7 (4H, m).

EXAMPLE 13

Preparation of Wettable Powders 30 parts ("part" stands for "part by weight" throughout the following description) of the Compound No. 3 were mixed with 2 parts of white carbon, and to the mixture further added 3 parts of sodium alkylethersulfate and 2 parts of sodium dialkylnaphthalenesulfonate acting as wetting agents. To the mixture was further added 63 parts of clay acting as a filler, and the admixture was mixed and then pulverized to prepare wettable powders.

EXAMPLE 14

Preparation of Emulsions

To 5 parts of the Compound No. 4 were added 15 parts of xylene and 75 parts of dimethylformamide, and further added 1.5 parts of polyoxyethylene alkyl ether, 2 parts of alkylbenzenesulfonate and 1.5 parts of polyoxyethylenesorbitanalkylate, the latter-mentioned three compounds acting as emulsifiers. The admixture was mixed to dissolve the Compound No. 4 to prepare an emulsion.

EXAMPLE 15

Preparation of Granules

To 8 parts of the Compound No. 1 were added 62 parts of clay and 26 parts of bentonite, and further added 0.5 parts of alkylbenzenesulfonate and 3.5 parts of sodium ligninsulfonate, the latter-mentioned two compounds acting as disintegrators. The mixture was mixed with an appropriate amount of water, and then granulated, dried and sieved to prepare granules.

EXAMPLE 16

Test for Appraisal of Effectiveness When Applied to
Rice Seedling by Spraying

Each test suspension of compounds of this invention was made by diluting with water the wettable powders prepared according to Example 13. It was sprayed with a spray gun in an amount of 10 ml per 1 pot to leaves of rice seedlings (Species: KOSHIHIKARI) of 4-leaf stage grown in 4 synthetic resin nursery pots each having a diameter of 6.5 cm. After drying by air, the pots were placed in a humidified chamber maintained at 25° C. and inoculated with rice blast fungus spores by spraying a suspension of rice blast fungus spores uniformly on the leaves of the rice plants. After placing the pots in the humidified chamber for one night, the pots were transferred into a room in which the environment was controlled artificially. After the lapse of 7 days from the inoculation, the number of lesions was counted and the preventive value was calculated from the following equation.

Preventive Value (%) =

$$\left[ 1 - \frac{\text{Average Number of Lesions Found in Treated Plot}}{\text{Average Number of Lesions Found in Untreated Plot}} \right] \times 100$$

The results are shown in Table 2.

TABLE 2

| Tested Compound No. | Concentration (ppm) | Preventive Value (%) | Chemical Damage to Rice Plant |
|---|---|---|---|
| 1 | 100 | 97 | None |
| 2 | 100 | 96 | None |
| 3 | 100 | 95 | None |
| 4 | 100 | 99 | None |
| 5 | 100 | 98 | None |
| 6 | 100 | 97 | None |
| 7 | 100 | 98 | None |
| 8 | 100 | 97 | None |
| 9 | 100 | 99 | None |
| 10 | 100 | 96 | None |
| 11 | 100 | 98 | None |
| 12 | 100 | 96 | None |
| Untreated Plot | — | 0 | |

EXAMPLE 17

Test for Appraisal of Effectiveness When Applied to Soil

Rice plants in seedling stage were raised to reach the 3-leaf stage in a similar manner to Example 16. Each test suspension of compounds of this invention was poured in an amount of 10 ml per 1 pot onto the soil in 4 synthetic resin nursery pots per plot having rice seedlings (Species: KOSHIHIKARI) of 3-leaf stage. After the lapse of 14 days from the pouring, the leaves were inoculated with rice blast fungus spores. After the lapse of 7 days from the inoculation, the number of lesions was counted and the preventive value was calculated from the counted number.

The results of the test are shown in Table 3.

TABLE 3

| Tested Compound No. | Concentration (ppm) | Preventive Value (%) | Chemical Damage to Rice Plant |
| --- | --- | --- | --- |
| 1 | 50 | 98 | None |
| 2 | 50 | 99 | None |
| 3 | 50 | 100 | None |
| 4 | 50 | 97 | None |
| 5 | 50 | 100 | None |
| 6 | 50 | 98 | None |
| 7 | 50 | 98 | None |
| 8 | 50 | 98 | None |
| 9 | 50 | 100 | None |
| 10 | 50 | 95 | None |
| 11 | 50 | 100 | None |
| 12 | 50 | 100 | None |
| Untreated Plot | — | 0 | |

The compounds of this invention are thus seen to be effective to prevent rice blast, which is a serious problem in growing of rice, for a long time without damaging the rice plants. They exhibit marked effectiveness for the prevention of the spread of rice blast, either by foliar application or by application to soil (including application on the surface of the water on a paddy field). Accordingly, the compounds of this invention are of great practical utility.

We claim:

1. A benzoisothiazole oxime represented by the following formula (I):

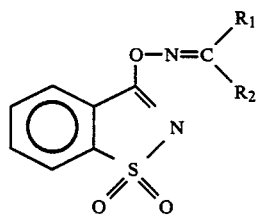

wherein $R^1$ is a $C_{1-6}$ alkyl group, and $R_2$ is a $C_{2-4}$ alkenyl, methoxymethyl, ethoxymethyl 2-methoxyethyl, methoxycarbonyl or ethoxycarbonyl.

2. The benzoisothiazole according to claim 1, wherein said benzolsothiazole is 3-(1-methoxycarbonyl-1-ethaneiminoxy)-1,2-benzoisothiazole 1,1-dioxide.

3. The benzoisothiazole according to claim 1, wherein said benzoisothiazole is 3-(5-hexene-2-iminoxy)-1,2-benzoisothiazole 1,1-dioxide.

4. The benzoisothiazole according to claim 1, wherein said benzoisothiazole is 3-(1-methoxy-2-propaneiminoxy)-1,2-benzoisothiazole 1,1-dioxide.

5. The benzoisothiazole according to claim 1, wherein said benzoisothiazole is 3-(3-butene-2-iminoxy)-1,2-benzoisothiazole 1,1-dioxide.

6. A plant protection agent for control of fungi and bacteria containing, as an effective component, at least one benzoisothiazole oxime represented by the following formula (I):

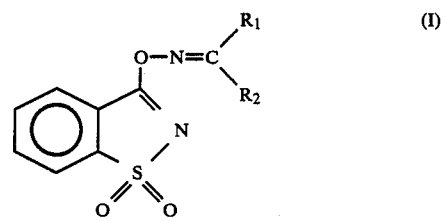

wherein $R_1$ is a $C_{1-6}$ alkyl group, and $R_2$ is a $C_{1-6}$ alkyl, a $C_{2-4}$ alkenyl, methoxymethyl, ethoxymethyl, 2-methoxymethyl, methoxycarbonyl, or ethoxycarbonyl, or $R_1$ and $R_2$ together form a cyclopentylidene or cyclohexylidene radical together with the C to which they are attached, and an inert diluent or filler.

7. The plant protection agent for control of fungi and bacteria according to claim 6, wherein said effective component is 3-(2-propaneiminoxy)-1,2-benzoisothiazole 1,1-dioxide.

8. The plant protection agent for control of fungi and bacteria according to claim 6, wherein said effective component is 3-(2-butaneiminoxy)-1,2-benzoisothiazole 1,1-dioxide.

9. The plant protection agent for control of fungi and bacteria according to claim 6, wherein said effective component is 3-(3-methylbutane-2-iminoxy)-1,2-benzoisothiazole 1,1-dioxide.

10. The plant protection agent for control of fungi and bacteria according to claim 6, wherein said effective component is 3-(4-methylpentane-2-iminoxy)-1,2-benzoisothiazole 1,1-dioxide.

11. The plant protection agent for control of fungi and bacteria according to claim 6, wherein said effective component is 3-(1-methoxycarbonyl-1-ethaneiminoxy)-1,2-benzoisothiazole 1,1-dioxide.

12. The plant protection agent for control of fungi and bacteria according to claim 6, wherein said effective component is 3-(5-hexene-2-iminoxy)-1,2-benzoisothiazole 1,1-dioxide.

13. The plant protection agent for control of fungi and bacteria according to claim 6, wherein said effective component is 3-(3,3-dimethylbutane-2-iminoxy)-1,2-benzoisothiazole 1,1-dioxide.

14. The plant protection agent for control of fungi and bacteria according to claim 6, wherein said effective component is 3-(1-methoxy-2-propaneiminoxy)-1,2-benzoisothiazole 1,1-dioxide.

15. The plant protection agent for control of fungi and bacteria according to claim 6, wherein said effective component is 3-(cyclopentaneiminoxy)-1,2-benzoisothiazole 1,1-dioxide.

16. The plant protection agent for control of fungi and bacteria according to claim 6, wherein said effective component is 3-(cyclohexaneiminoxy)-1,2-benzoisothiazole 1,1-dioxide.

17. The plant protection agent for control of fungi and bacteria according to claim 6, wherein said effective component is 3-(3-pentaneiminoxy)-1,2-benzoisothiazole 1,1-dioxide.

18. The plant protection agent for control of fungi and bacteria according to claim 6, wherein said effective component is 3-(3-butene-2-iminoxy)-1,2-benzoisothiazole 1,1-dioxide.

19. A method of prevention of rice blast, comprising applying an effective amount to a rice seeding or to soil in which it grows of at least one benzoisothiazole oxime represented by the following formula (I):

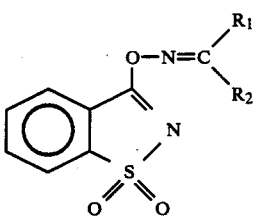

wherein $R_1$ is a $C_{1-6}$ alkyl group, and $R_2$ is a $C_{1-6}$ alkyl, a $C_{2-4}$ alkenyl, methoxymethyl, ethoxymethyl, 2-methoxymethyl, methoxycarbonyl, or ethoxycarbonyl, or $R_1$ and $R_2$ together form a cyclopentylidene or cyclohexylidene radical together with the C to which they are attached.

20. The method according to claim 19, wherein said benzoisothiazole is 3-(2-propaneiminoxy)-1,2-benzoisothiazole 1,1-dioxide.

21. The method according to claim 19, wherein said benzoisothiazole is 3(2-butaneiminoxy)-1,2-benzoisothaizole 1,1-dioxide.

22. The method according to claim 19, wherein said benzoisothiazole is 3-(3-methylbutane-2-iminoxy)-1,2-benzoisothiazole 1,1-dioxide.

23. The method according to claim 19, wherein said benzoisothiazole is 3-(3-methylpentane-2-iminoxy)-1,2-benzoisothiazole 1,1-dioxide.

24. The method according to claim 19, wherein said benzoisothiazole is 3-(1-methoxycarbonyl-1-ethaneiminoxy)-1,2-benzoisothiazole 1,1-dioxide.

25. The method according to claim 19, wherein said benzoisothiazole is 3(5-hexene-2-iminoxy)-1,2-benzoisothiazole 1,1-dioxide.

26. The method according to claim 19, wherein said benzoisothiazole is 3(3,3-dimethylbutane-2-iminoxy)-1,2-benzoisothiazole 1,1-dioxide.

27. The method according to claim 19, wherein said benzoisothiazole is 3(1-methoxy-2-propaneiminoxy)-1,2-benzoisothiazole 1,1-dioxide.

28. The method according to claim 19, wherein said benzoisothiazole is 3-(cyclopentaneiminoxy)-1,2-benzoisothiazole 1,1-dioxide.

29. The method according to claim 19, wherein said benzoisothiazole is 3(cyclohexaneiminoxy)-1,2-benzoisothiazole 1,1-dioxide.

30. The method according to claim 19, wherein said benzoisothiazole is 3-(3-pentaneiminoxy)-1,2-benzoisothiazole 1,1-dioxide.

31. The method according to claim 19, wherein said benzoisothiazole is 3-(3-butene-2-iminoxy)-1,2-benzoisothiazole 1,1-dioxide.

* * * * *

UNITED STATES PATENT AND TRADEMARK OFFICE
CERTIFICATE OF CORRECTION

PATENT NO.   : 4,855,311
DATED        : August 08, 1989
INVENTOR(S)  : Shinobu IRIUCHIJIMA, et al It is certified that error appears in the above-identified patent and that said Letters Patent is hereby corrected as shown below:

On the Title Page, Item [73], the name of the second assignee is incorrect. It should read as follows:

--DENKI KAGAKU KOGYO KABUSHIKI KAISHA--

Signed and Sealed this

Twenty-sixth Day of June, 1990

*Attest:*

HARRY F. MANBECK, JR.

*Attesting Officer*  *Commissioner of Patents and Trademarks*